(12) United States Patent
Kuronen et al.

(10) Patent No.: US 8,632,981 B2
(45) Date of Patent: Jan. 21, 2014

(54) METHOD FOR A RAPID TEST

(75) Inventors: Ilpo Kuronen, Kuopio (FI); Ilkka Mononen, Turku (FI); Markku Parviainen, Karttula (FI)

(73) Assignee: Oy Reagena Ltd., Toivala (FI)

( * ) Notice: Subject to any disclaimer, the term of this patent is extended or adjusted under 35 U.S.C. 154(b) by 942 days.

(21) Appl. No.: 11/502,785

(22) Filed: Aug. 10, 2006

(65) Prior Publication Data

US 2006/0275754 A1 Dec. 7, 2006

Related U.S. Application Data

(63) Continuation of application No. PCT/FI2005/000081, filed on Feb. 9, 2005.

(30) Foreign Application Priority Data

Feb. 11, 2004 (FI) .................................... 20040205

(51) Int. Cl.
*G01N 33/53* (2006.01)
(52) U.S. Cl.
USPC ........................................... 435/7.1; 435/7.2
(58) Field of Classification Search
USPC ................................ 422/82.05, 100, 102, 104
See application file for complete search history.

(56) References Cited

U.S. PATENT DOCUMENTS

| 5,571,726 A | 11/1996 | Brooks, Jr. et al. | 436/525 |
| 5,712,170 A | 1/1998 | Kouvonen et al. | 436/518 |
| 6,080,551 A | 6/2000 | Doyle et al. | 435/7.4 |
| 2003/0082587 A1* | 5/2003 | Seul et al. | 435/6 |
| 2003/0148384 A1 | 8/2003 | Whiting | 435/7.1 |

FOREIGN PATENT DOCUMENTS

| EP | 0 724 909 A1 | 8/1996 |
| EP | 0 291 194 B2 | 7/2003 |
| EP | 1 369 473 A2 | 12/2003 |
| EP | 0 299 428 B2 | 1/2004 |
| WO | WO 89/06801 | 7/1989 |
| WO | WO 92/01226 | 1/1992 |
| WO | WO 97/38311 | 10/1997 |
| WO | WO 2005078446 A1 * | 8/2005 |

OTHER PUBLICATIONS

Branson, B.M., Point-of-Care Rapid Tests for HIV Antibodies, J Lab Med 2003, pp. 288-295, vol. 27.

* cited by examiner

*Primary Examiner* — Jacob Cheu
(74) *Attorney, Agent, or Firm* — Harrington & Smith

(57) ABSTRACT

Disclosed is a method for a rapid test. In accordance with an embodiment, a particle reagent is placed into a separate sample or reagent receptacle or test tube, in which the particle reagent reacts with one or several analytes in the liquid sample, and the particle reagent is put into contact with the rapid test device, in which a visible signal is formed by the particle reagent.

8 Claims, 2 Drawing Sheets

METHOD FOR A RAPID TEST

This application is a continuation of International Patent Application No. PCT/FI2005/000081 filed on Feb. 9, 2005.

The present invention relates to a method for a rapid test.

BACKGROUND OF THE INVENTION

Rapid tests are generally used devices for qualitative purposes. The popularity of the rapid tests is based on the fact that they are easy-to-use, fast and inexpensive. The function of the rapid test is based on principles presented, for example in patent publications WO 92/01226 and U.S. Pat. No. 5,712,170. The device mentioned in these examples is based on membrane material, which contain all the reagents needed for analyzing a test in such a way that the particle reagent needed for the test is placed on the test strip so that the sample placed on the strip moves in the strip system and dissolves the particle reagent by means of liquid flow. After this, the sample and the particle reagent move ahead in the strip system by means of capillary forces. Molecules attached to the membrane structure bind the particle reagent by the sample, thus forming a coloured figure on the membrane. This principle is presented in many publications, which present the particle reagent placed on the test strip, from which it reacts and moves ahead in the membrane-like structure by means of capillary forces.

Placing the particle reagent in the test structure is useful in applications, in which the most basic properties of the rapid test are that it is user-friendly and it can be industrially copied. On the other hand, the particle reagent placed in the test structure causes significant measuring inaccuracy due to the non-simultaneous detachment and dissolution of the particle reagent. This phenomenon is generally seen especially in those rapid tests that use blood or blood derivatives as samples.

In order to make the rapid tests quantitative, optical reading instruments that are able to convert the intensity of the formed line into a numerical value are used. By comparing the intensity of the formed line to the standard value entered in advance to the device, the device can then conclude the quantity of the substance under measurement in the sample. This technique enables in part quantitative measurements with rapid tests, but it cannot take into account the changes in the preparation and making of the tests, which directly cause inaccuracy to the result. The optical readers used at present can be based on CD camera technique, measuring of reflected light or of fluorescence. In present techniques, the reading of the result may be done by forming a ratio by means of the formed test line in the test strip and control line, and by calculating the result by means of a value entered in advance. However, this technique is also incapable of taking into account the variation among sets of tests in which case the result of the analysis can be inaccurate or false.

The patent application US 2003/0148384 presents a method, in which the rapid test device has been improved by adding a particle reagent into a receptacle, from which it dissolves into the sample under analysis, and flows into the test device after the analysed sample. In the present method, the sample under analysis has to be a particle-like in order for the described method to work. By means of the described method, it is possible to reach a higher analytical sensitivity with particle-like analytes. The method in question does not make it possible to measure the molecules for analysis, which are dissolved in liquid, because in the described method, the particle reagent does not flow into the test device simultaneously with the subject under measurement.

The U.S. Pat. No. 6,080,551 describes an application, in which, by means of a test device, observations are made of different GST protein variants by using labelled particle reagent suspension. In the described technique, a particle reagent is in a solution in a receptacle, in which it reacts with the analyte. In the method, the particle reagent is in liquid form, and it is added in the receptacle with the sample when the test device is used. Due to this, the stability of the particle reagent in long-term storage is very limited, and it has to be added separately to the reacting mixture when the test device is used.

The U.S. Pat. No. 5,571,726 describes a method for preparation of a particle reagent by means of glutaraldehyde. The basic reagent in the method is glutaraldehyde, which forms protein binding chemical groups in the particle. However, said glutaraldehyde is not a necessary element when preparing heavy metal particles since the negatively charged surface of the particles binds itself proteins by strong ionic bonds without glutaraldehyde.

The object of the invention is to present a method for preparing a rapid test, which increases the reliability of the results obtained from the rapid tests, and enables more accurate quantitative measurement than before.

DESCRIPTION OF THE INVENTION

In the method, which is the object of the invention, the particle reagent is placed into a separate test tube, or sample or reagent receptacle or a corresponding container where a liquid sample containing one or several analytes reacts with the particle reagent, and from which the particle reagent is put into contact with the rapid test device, in which the reagent in question flows ahead and forms a visible signal. The particle reagent is put into contact with the test device either by transferring the reagent from the said receptacle or corresponding either entirely or partially into the rapid test device, or by bringing the rapid test device in the receptacle and by putting it into contact, in a suitable way, with the particle reagent in the receptacle. In the method in accordance with the invention the particle reagent is made to react with the sample in a constant amount and -concentration, which enables more accurate analysis of the sample than before. In the method, the particle reagent flows into the analytic device simultaneously with the subject under measurement.

In the method in accordance with the invention, the used particle reagent can be prepared with any method, which produces particles labelled with proteins or other molecules.

In an advantageous application of the invention, the particle suspension or particle reagent in dry form is put in the reagent or sample receptacle. When the particle reagent is in dry form it remains viable even for several years. Therefore, by the method, which is the object of the invention, a longer viability for the particle reagent can be reached than before.

In another advantageous application of the invention, the said particle reagent is dissolved into liquid form by means of a sample or one or several other liquids or combination of them. After this the, the liquid particle reagent is transferred with a device meant for transferring liquid into the rapid test device, or it is absorbed directly from the said receptacle or test tube into the rapid test device, into which bound molecules as well as particle reagent enable the forming of coloured figures in the test. The method in accordance with the invention is especially beneficial in cases where the intensity of the colour of the figure formed in the rapid test is meant to correspond either directly or indirectly to the amount of the substance under measurement in the sample.

In another advantageous additional application of the invention, the particle reagent made into soluble form is made to react with the substance under measurement, which may be protein, polypeptide, carbohydrate, bacteria or virus, or parts or mixtures of them. The reaction between the subject molecules and particle reagent takes place in a test tube or another reaction container and it happens in constant volume and— circumstances, which enable the making of a more accurate analysis than before.

In another advantageous additional application of the invention, the particle reagent is prepared from heavy metal or plastics as well as bioactive molecules, which are bound to them.

In another advantageous additional application of the invention, the particles of the particle reagent are 10 nm-1000 nm in size, and the molecules conjugated with it are proteins, polysaccharides, haptens, or polypeptides, or mixtures of them. By means of reagents having small particle size, higher analytical sensitivity is achieved.

In another advantageous additional application of the invention, the rapid test is enclosed in a frame, cartridge or other structure. As a result, the usability of the test strip improves because the frame forms a structure, which is durable and easy to handle, around the rapid test.

DESCRIPTION OF THE DRAWINGS

Next, the method in accordance with the invention is explained in more detail with reference to the accompanying figure, in which.

The rapid test 100 presented in the figures includes an analysis membrane 101, a sample membrane 107, an adsorbent membrane and, in the advantageous application, a support. The analysis membrane or test membrane 101 in the rapid test is prepared from nitrocellulose, nylon, polystyrene, or cellulose in these applications. The sample and adsorbent membranes of the rapid test are, in turn, advantageously made of cellulose, glass fibre, polystyrene, nitrocellulose, nylon or of any other material that adsorbs liquid. The device includes a support of the rapid test, which is of any material, on which the analysis, absorbent or sample membranes are attached. Advantageously, the support is made of polystyrene or polyvinyl derivatives, and it contains an adhesive for attaching the membranes.

Figure 1:
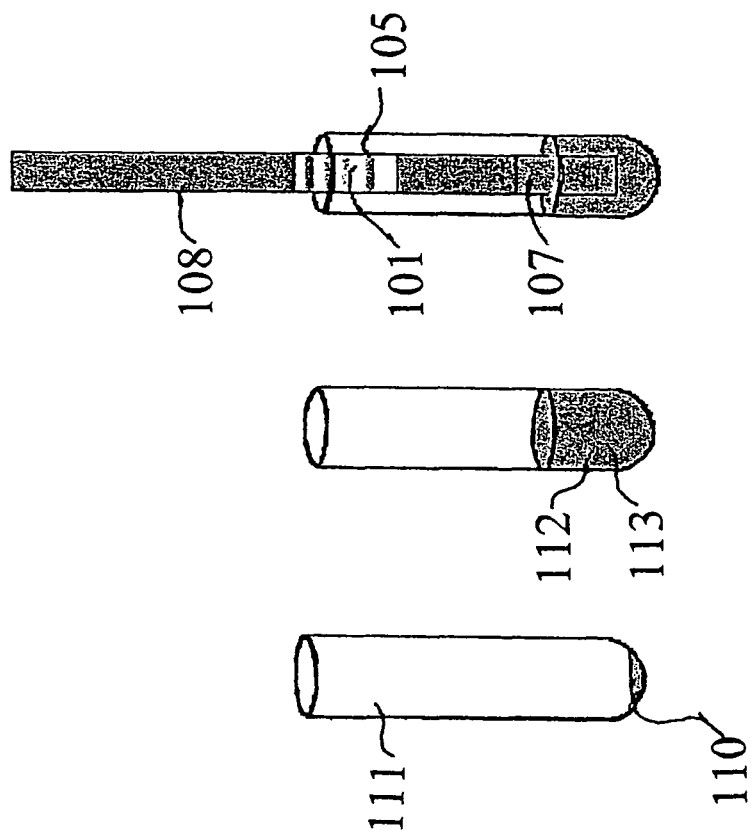
FIG. 1 shows an application of the method in accordance with the invention as a principle figure viewed from the side.

FIG. 1 shows an application of method in accordance with the invention. In this application the test line formed in the rapid test is accomplished with the gold particle suspension 110, into which an antigen or antibody, which is conjugated with the substance under measurement, is attached. The gold particle suspension is placed into-the-test tube 111, into which the analyte 112 is added, as well as, if necessary, analysis liquid 113. During analysis, the rapid test is placed into the test tube with the sample membrane 107 first. The sample membrane absorbs itself liquid from the test tube, and transfers it onto the analysis membrane 101, and from there onwards, to the absorbent membrane 108. The antigen or antibody on the analysis membrane, at the point of the test line, binds the substance under measurement from the liquid, into which substance the antigen or antibody in the gold particles binds itself. The result from this is the formation of the coloured test line 105, the intensity of the colour of which depends either directly or indirectly from the concentration of the substance under measurement. Naturally, another, suitable for the purpose, particle reagent can be used in other applications.

Figure 2:
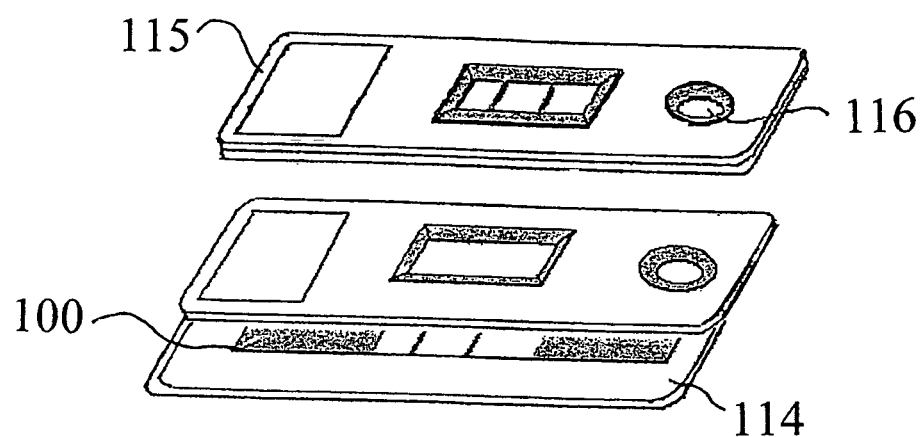
FIG. 2 shows an application of the rapid test in accordance with the invention.

FIG. 2 presents an application in accordance with the invention, in which the rapid test 100 is placed between the plastic cartridges 114 and 115, which forms a test device 116 inside a cartridge or capsule. When using the test device 116 inside the cartridge, the sample is added into a separate test tube or receptacle 111, which includes the particle reagent 110. The sample and the particle reagent in soluble form are then transferred together into the sample well of the test device 116, after which the rapid test works in a previously known way.

Figure 3:
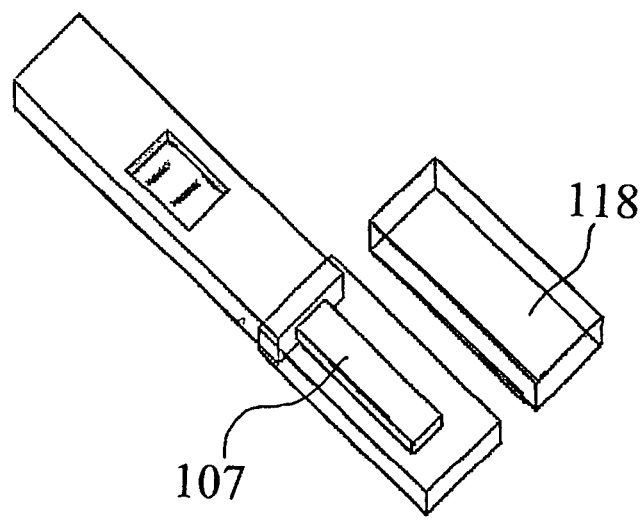
FIG. 3 shows an application of the test device in accordance with the invention.

FIG. 3 presents an application in accordance with the invention, in which the reagent receptacle 118 including the particle reagent is attached to the test device inside a cartridge. When the test device is used, the sample is added into the receptacle 118, from where the sample dissolves the particle reagent in dry form. After that, the reagent receptacle 118 is connected to the test device so that the liquid is absorbed to the sample membrane 107 or sampler of the test device, which sampler transfers the sample into the rapid test.

The analysis membrane can be made of any material that allows the liquid flow and binds antibodies or antigens, but in an advantageous application of the invention, the analysis membrane is made of cellulose, nitrocellulose, polyvinyl fluoride, nylon, or polystyrene having porosity greater than 5 nm.

The sample and adsorbent membrane may be made of any material that adsorbs liquid, but in an advantageous application of the invention, they are made of cellulose, glass fibre, nylon, or mixtures of them.

The method can be used for analysis and measurement of any substances that will bind to antibodies or antigens, but in an advantageous application of the invention, the substances under measurement are proteins, polypeptides, polysaccharides, virus particles, or bacteria, or mixtures of them.

EXAMPLE 1

Next, an example of the method and its use is presented when measuring a clinically important marker protein.

CRP is a very important clinical marker of measuring immunity and/or infection from blood samples. CRP can be measured by several known methods such as, turbidometric, EIA or fluorometric methods. What is common to these methods is that they are very equipment-bound, they require long making process and high expertise to do it. CRP is a protein molecule, the measurement of which always requires antibodies that bind to it, which antibodies may be polyclonal or monoclonal. The method and device in accordance with the present invention enable the measurement of CRP from a blood sample in an easy and fast way. In addition, the concentration of CRP can be evaluated with a suitable accuracy by ocular estimate without separate equipment. In an advantageous application of the invention the amount of CRP can be measured accurately in respect of the separate reading equipment based on a CD camera.

The gold particle suspension for preparing the CRP rapid test was made by reducing gold tetrachloride solution by citric acid solution. The gold particles were labelled with bovine serum albumen by adding 5 mM of boric acid (as final concentration) and 1 mg of bovine serum albumen per 100 ml of the particle suspension. After mixing for two hours, the gold particle suspension was concentrated by centrifugation of the particles to the bottom of the tube from where they were made to suspension back to the solution by means of deionised water. After this, particle suspensions of various content were made from concentrated gold particle suspension, the optic density of which particle suspensions was adjusted photometrically such that they were 1, 3, 9, 12 and 18 when measured by 520 nm wave length. The solutions in question were used for preparing narrow lines of approx. 1 mm in width and approx. 2 mm apart from each other on the nitrocellulose membrane, with the liquid dispenser manufactured by BioDot Ltd, (Millipore, USA). Immediately after dispensing, the membranes were dried at +50° C. temperature so that the lines remained as narrow stripes with desired length on the membrane. In order to prepare a test line, the gold particle suspension was labelled with CRP polyclonal antibody by adding 1 mg of purified antibody to the gold particle suspension. The labelled particle suspension was concentrated to the optic density of 5, as shown above. CRP strip was prepared onto the nitrocellulose membrane by dispensing a test line with CRP monoclonal antibody with the liquid dispenser manufactured by BioDot Ltd. The membrane was dried as presented above and attached to the support (G&L, USA). In addition, a sample membrane and absorbent membrane were placed onto the support such that the other edge of both membranes overlapped about 1 mm with the nitrocellulose membrane in order to allow liquid flow in membrane structure from the test tube through the nitrocellulose membrane to the absorbent pad. The labelled CRP antibody particle suspension was added 2% of sucrose, 1% of bovine serum albumen and 10 mM of phosphate buffer (all stated as final concentration). From this solution, 20 ml were dispensed to the test tubes and tubes were allowed to dry until the particle suspension had completely dried up to the bottom of the tubes. In order to find the standard lines with correct strength, different samples containing various concentrations of CRP were analysed by adding 0.5 ml of diluted phosphate buffer and 1 ml of serum sample into the test tubes. The tubes were mixed, and the CRP tests presented above were put into the test tubes. After 10 minutes, red lines appeared in the tests at the positions of the test lines, the intensity of which were dependent on the concentration of the CRP in the sample. By comparing test lines formed this way with the standard lines, the desired standard lines and their correspondence to the desired concentration of CRP could be concluded. After that, the test strip in accordance with FIG. 1 was prepared, which had the standard lines the optical density of which corresponded with values 2, 7 and 18 with 520 nm wavelength, and the test line. The concentrations of CRP, which corresponded to the standard lines, were 5 mg/l, 10 mg/l and 20 mg/l. By using CRP test strip prepared this way, known serum samples were analysed. These results are presented in table 1. Table 1 thus shows the result of the tests, which could be concluded with suitable accuracy by ocular estimate as well as accurately by using a device based on CD camera (Anibiotech, Finland), When calculating results on the basis of numerical values from the CD-camera, the results from the standard lines as well as concentrations of CRP corresponding to them, a straight line was drawn in X-Y function, the equation from which the result of the test line could be calculated.

EXAMPLE 2

Puumala virus—specific IgM antibody is generally used as a marker protein of acute nephropathia epidemica (NE), which is partitioned from a blood sample. In order to detect this marker protein, a rapid test demonstrating acute nephropathia epidemica was prepared in accordance with FIG. 1 by selecting optic densities of 1, 3 and 12 as standard lines, the correspondence of which to the reacting ability of the marker protein of acute nephropathia epidemica corresponded to the situations where the optic density 1 equalled uncertain finding, 3 for certain finding and 12 for high positive finding. The test line was prepared by dispensing genetically engineered Puumala virus antigen into the test strip, as in example 1. The particle suspension was prepared as in example 1 by conjugating the gold particle suspension to the purified human IgM antibody prepared in a rabbit. The particle suspension labelled with the antibody was dried in the test tube the same way as in example 1. The analysis of the samples was also carried out the same way as in example 1. When analysing known serum samples in accordance with the test strip for acute nephropathia epidemica in accordance with example 2, the finding could be classified as negative, uncertain, clearly positive and highly positive by ocular estimate. The results are presented in table 2. The results corresponded well to the results obtained by the commercial EIA method. Also when the results were read with a CD camera, the results were identical to those of the commercial EIA method. In this case the samples were classified in the above-presented classes on the basis of numerical values obtained by the CD camera from the standard lines.

EXAMPLE 3

When comparing method and device prepared in example 1 in accordance with the invention to the commercially accessible CRP rapid test (Medix Biochemica, Finland), it was observed that the method and device in accordance with the invention were able to measure clearly more accurately the changes in CRP values. Especially, with concentrations of CRP which varied in the range of 5 mg/l-20 mg/l, the measuring accuracy of the commercial method did not have the sufficient distinguishing ability whereas, with the method in accordance with the invention, the levels between 5 mg/l to 10 mg/l as well as between 10 mg/l and 20 mg/l, could be distinguished. In this example, the reading of both tests was done by ocular estimate.

The invention is not limited to the presented advantageous applications, but it can vary within the limits of the inventive idea formed in the claims.

TABLE 1

| Concentration using the comparison method (mg/l) | Result from test strip, ocular estimate (mg/l) | Result from reading device (mg/l) |
|---|---|---|
| 3.6 | <5 | 4.1 |
| 2.4 | <5 | 2.8 |
| 1.3 | <5 | 1.9 |
| 1.7 | <5 | 1.1 |
| 8.9 | 5-10 | 9.6 |
| 1 | <5 | 1.6 |
| 9.3 | 5-10 | 10.9 |
| 10.8 | 10-20 | 12.6 |
| 19.2 | 10-20 | 17.2 |
| 18.8 | 10-20 | 15.2 |
| 28.1 | >20 | 21.2 |
| 22.8 | >20 | 29.3 |
| 22.7 | >20 | 25 |
| 32.8 | >20 | 41.6 |
| 39.6 | >20 | 38.8 |
| 35.3 | >20 | 34.4 |
| 37.3 | >20 | 36.4 |
| 31.1 | >20 | 28.8 |
| 340 | >20 | >189 |
| 263 | >20 | >189 |
| 189 | >20 | 187 |

TABLE 2

| SAMPLE ID | IgM-Elisa (1) (Progen) index (Q) (2) | Result | RESULTS (Posit/Equiv/Negat) Result |
|---|---|---|---|
| 1 | 2.9 | Posit (+) | Posit (+) |
| 2 | 0.2 | Negat (−) | Negat (−) |
| 3 | 1.4 | Equiv (+/−) | Equiv (+/−) |
| 4 | 3.4 | Posit (+) | Posit (+) |
| 5 | 0.3 | Negat (−) | Negat (−) |
| 6 | 2.1 | Posit (+) | Posit (+) |
| 7 | 1.1 | Equiv (+/−) | Equiv (+/−) |
| 8 | 0.7 | Negat (−) | Negat (−) |
| 9 | 0.3 | Negat (−) | Negat (−) |
| 10 | 0.1 | Negat (−) | Negat (−) |
| 11 | 3.3 | Posit (+) | Posit (+) |
| 12 | 0.3 | Negat (−) | Negat (−) |
| 13 | 1.0 | Equiv (+/−) | Equiv (+/−) |
| 14 | 3.8 | Posit (++) | Posit (++) |
| 15 | 0.3 | Negat (−) | Negat (−) |
| 16 | 0.3 | Negat (−) | Negat (−) |
| 17 | 1.0 | Equiv (+/−) | Equiv (+/−) |
| 18 | 3.6 | Posit (++) | Posit (++) |
| 19 | 0.4 | Negat (−) | Negat (−) |
| 20 | 3.0 | Posit (+) | Posit (+) |
| 21 | 0.5 | Negat (−) | Equiv (+/−) |
| 22 | 2.6 | Posit (+) | Posit (+) |
| 23 | 0.3 | Negat (−) | Negat (−) |
| 24 | 3.9 | Posit (+) | Posit (+) |
| 25 | 1.8 | Equiv (+/−) | Posit (+) |
| 26 | 3.9 | Posit (+) | Posit (+) |
| 27 | 0.3 | Negat (−) | Negat (−) |
| 28 | 3.4 | Posit (++) | Posit (++) |
| 29 | 3.0 | Posit (+) | Posit (+) |
| 30 | 2.8 | Posit (+) | Posit (+) |
| 31 | 0.3 | Negat (−) | Negat (−) |
| 32 | 1.6 | Equiv (+/−) | Posit (+) |
| 33 | 4.4 | Posit (+) | Posit (+) |
| 34 | 1.3 | Equiv (+/−) | Posit (+) |
| 35 | 0.2 | Negat (−) | Negat (−) |
| 36 | 0.5 | Negat (−) | Negat (−) |
| 37 | 1.2 | Equiv (+/−) | Equiv (+/−) |
| 38 | 0.3 | Negat (−) | Negat (−) |
| 39 | 4.2 | Posit (+) | Posit (+) |
| 40 | 0.3 | Negat (−) | Negat (−) |

The invention claimed is:

1. A method for a rapid test, comprising:
preparing a particle reagent by dispensing a liquid suspension of labelled reagent particles comprising heavy metal or plastic particles into a test tube or receptacle separate from a rapid test device, allowing said liquid particle suspension to dry until the particle suspension is completely dried up to a bottom of the receptacle or the test tube to obtain a dried particle reagent in the test tube or the receptacle,
before the rapid test, the dried particle reagent is made into soluble form by adding a liquid sample with one or several analytes on the dried particle, whereby the dried particle reagent resolubiizes and reacts with the one or several analytes in the sample, and
the particle reagent and the one or several analytes bound to the particle reagent are transferred into contact with a separate rapid test device, in which a visible signal is formed by the particle reagent, wherein particles of the particulate reagent are about 10 nm to about 1000 nm in size.

2. The method in accordance with claim 1, wherein, the dried particle reagent is made into soluble form by adding the liquid sample with one or several analytes on the dried particle, in the same test tube or receptacle of the dried particulate reagent.

3. The method in accordance with claim 1, wherein, the dried particle reagent is made into soluble form by adding the liquid sample with one or several analytes on the dried particle, in the same test tube or receptacle of the dried particulate reagent.

4. The method in accordance with claim 1, wherein the dried labelled particle reagent comprises particulate plastic particles.

5. The method in accordance with claim 1, wherein the liquid suspension of labelled reagent particles comprises plastic particles.

6. The method in accordance with claim 1, wherein particles of the particulate reagent are about 250 nm to about 1000 nm in size.

7. The method in accordance with claim 1, wherein the wherein particles of the particulate reagent are about 250 nm to about 1000 nm in size.

8. A method for a rapid test, comprising:
preparing a particle reagent by dispensing a liquid suspension of labelled reagent particles comprising heavy metal or plastic particles into a test tube or receptacle separate from a rapid test device, allowing said liquid particle suspension to dry until the particle suspension is completely dried up to a bottom of the receptacle or the test tube to obtain a dried particle reagent in the test tube or the receptacle,
before the rapid test, the dried particle reagent is made into soluble form by adding a liquid sample with one or several analytes on the dried particle, whereby the dried particle reagent resolubiizes and reacts with the one or several analytes in the sample, and
the particle reagent and the one or several analytes bound to the particle reagent are transferred into contact with a separate rapid test device, in which a visible signal is formed by the particle reagent, wherein particles of the particulate reagent are about 500 nm to about 1000 nm in size, and wherein the test tube or receptacle and the rapid test device are separate from each other and handled separately until the particle reagent is put into contact with the rapid test device.

\* \* \* \* \*